United States Patent [19]
Herskowitz

[11] Patent Number: 5,348,539
[45] Date of Patent: Sep. 20, 1994

[54] INFUSION PUMP FOR USE WITH PREPACKAGED IV BAGS

[76] Inventor: Glenn Herskowitz, 425 Divisadero, Suite 200, San Francisco, Calif. 94117

[21] Appl. No.: 84,527
[22] Filed: Jun. 29, 1993
[51] Int. Cl.⁵ .......................................... A61M 5/142
[52] U.S. Cl. .................................. 604/141; 604/153
[58] Field of Search ............... 604/141, 153, 140, 132; 128/DIG. 12

[56] References Cited

U.S. PATENT DOCUMENTS

| | | | |
|---|---|---|---|
| 3,507,278 | 4/1970 | Werding | 604/141 |
| 3,640,277 | 2/1972 | Adelberg | 604/141 |
| 3,895,741 | 7/1975 | Nugent | 604/141 |
| 4,684,367 | 8/1987 | Schaffer et al. | 604/141 |
| 4,735,613 | 4/1988 | Bellin et al. | 604/141 |
| 5,045,064 | 9/1991 | Idriss | 604/132 |
| 5,059,182 | 10/1991 | Lang | 604/141 |
| 5,088,983 | 2/1992 | Burke | 604/141 |
| 5,106,374 | 4/1992 | Apperson | 604/140 |
| 5,135,499 | 8/1992 | Tafani et al. | 604/141 |
| 5,163,909 | 11/1992 | Stewart | 604/140 |
| 5,176,644 | 1/1993 | Srisathapat | 604/141 |
| 5,207,645 | 5/1993 | Ross | 604/141 |

*Primary Examiner*—Paul J. Hirsch
*Attorney, Agent, or Firm*—Flehr, Hohbach, Test, Albritton & Herbert

[57] ABSTRACT

An infusion pump for use with standard pre-filled single dose IV bags. The pump includes an inflatable chamber having a diaphragm which expands under fluid pressure to compress the sidewalls of an IV bag. A fluid is directed under pressure to the chamber for causing it to inflate under influence of a control system. In one embodiment the fluid comprises a liquid which is transferred to and from the chamber from a reservoir. In another embodiment the fluid comprises a gas.

17 Claims, 8 Drawing Sheets

5,348,539

INFUSION PUMP FOR USE WITH PREPACKAGED IV BAGS

BACKGROUND OF THE INVENTION

1. Field of the Invention

This invention relates in general to methods and apparatus for infusing intravenous ("IV") solutions. In particular, the invention relates to an infusion pump which is adapted for use with prepackaged, single dose containers for delivering solutions intravenously to patients.

2. Description of the Prior Art

Infusion pumps are used to deliver various types of solutions intravenously to patients. A variety of drugs are commonly administered to patients by means of the intravenous solutions. Among the types of therapies requiring this kind of administration are chemotherapy, antibiotic therapy and antiviral therapy. In many cases, patients receive multiple daily therapies. Certain medical conditions require infusions of drugs in solution over relatively short periods such as from 30 minutes to 2 hours. It is important that the solutions be administered accurately and completely.

The different types of infusion pumps in the prior art include elastomeric pumps which squeeze the solution from flexible containers, such as balloons, into tubing for delivery to the patient. Spring loaded pumps have also been provided to pressurize the solution containers or reservoirs. Infusion pumps have also been provided with cartridges containing flexible compartments that are squeezed by pressure rollers for discharging the solutions, such as the pump shown in U.S. Pat. No. 4,741,736. These types of infusion pumps, however, require special containers and are not adaptable for using standard pre-filled single dose containers for IV solutions. Where infusion pumps cannot use the standard pre-filled single dose containers, it is necessary to separately compound the solution in large containers and transfer portions to the cartridges, balloons, reservoirs and other specialized containers. The requirement to compound and transfer the IV solution is time consuming, and because the work must be done by professionals, the cost is increased to the consumer. In addition, the requirement to manipulate the solutions and medications increases the risk of contamination in the preparation phase. This process also creates storage problems in that the compounded solution must be refrigerated, which further adds to the cost. The need has therefore been recognized for an infusion pump system which obviates the limitations and disadvantages of existing pumps of this type, and which is adapted for use with standard pre-filled single dose IV containers.

OBJECTS AND SUMMARY OF THE INVENTION

It is a general object of the invention to provide a new and improved infusion pump which is adapted for use with pre-filled single dose IV containers.

Another object is to provide an infusion pump of the type described which eliminates the need for the health care professional to separately compound and transfer the IV solution into containers used with the pump, and thereby minimize costly preparation steps.

Another object is provide an infusion pump of the type described which accurately dispenses the IV solution at a controlled pressure and for a controlled period of time.

Another object is to provide an infusion pump of the type described which includes a control system with safety features.

Another object is to provide an infusion pump of the type described which achieves health benefits by obviating the risk of contaminating the IV solution, obviating the need for refrigeration of the solution, and providing an alarm in the case where the solution is not completely delivered to the patient.

The invention in summary provides an infusion pump having a compartment for receiving a standard pre-filled single dose IV container bag. An inflatable chamber is provided with a diaphragm which is juxtaposed with a sidewall bag. For initiating the delivery mode of operation, a fluid is pumped into the chamber so that the diaphragm expands and compresses the bag sidewalls. Intravenous solution contained within the bag is thereby pressurized and forced out through a dispensing port into IV tubing for delivery to the patient. A control system includes means for rapid filling of the chamber during an initial phase of the delivery mode followed by higher pressure delivery of the fluid into the chamber for compressing the bag sidewalls. The solution dispensing rate is controlled responsive to the pressure of the solution being dispensed to the port by means of a sensor which indirectly senses the solution pressure.

The foregoing and additional objects and features of the invention will appear from the following specification in which the several embodiments have been set forth in detail in conjunction with the accompanying drawings.

DESCRIPTION OF THE PREFERRED EMBODIMENTS

Figure 1:
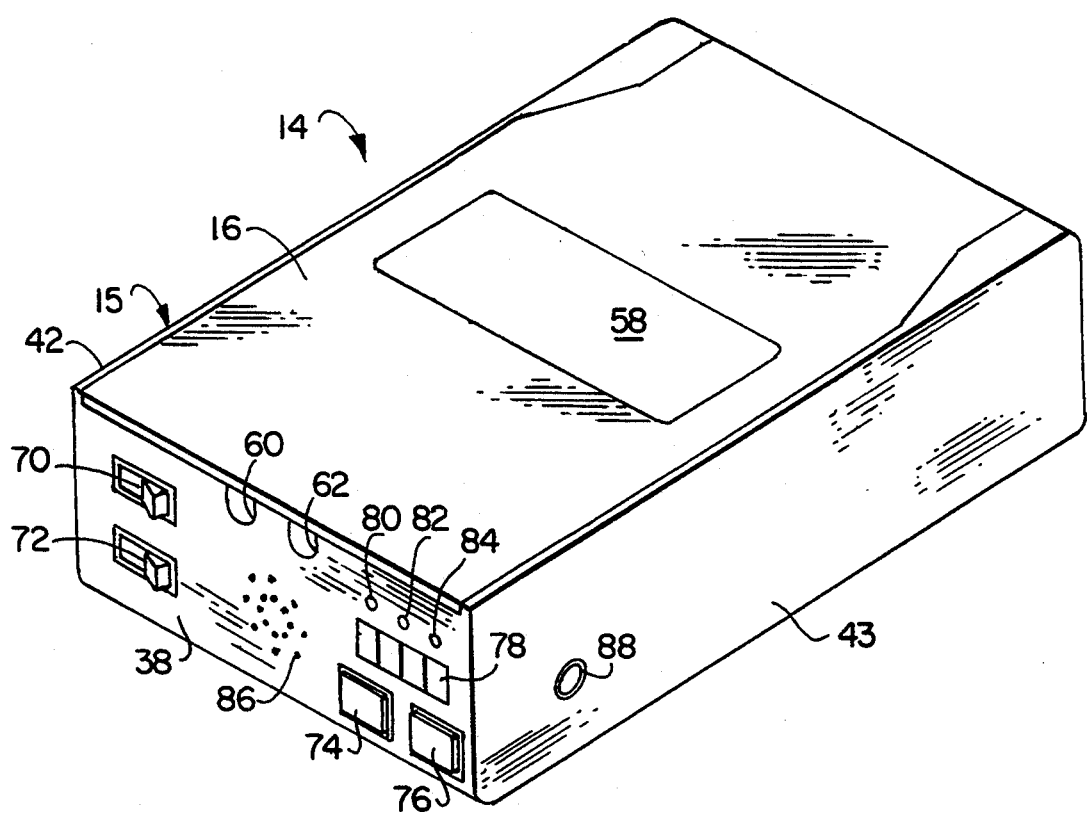
FIG. 1 is a perspective view illustrating the infusion pump in accordance with one embodiment of the invention.
Figure 2:
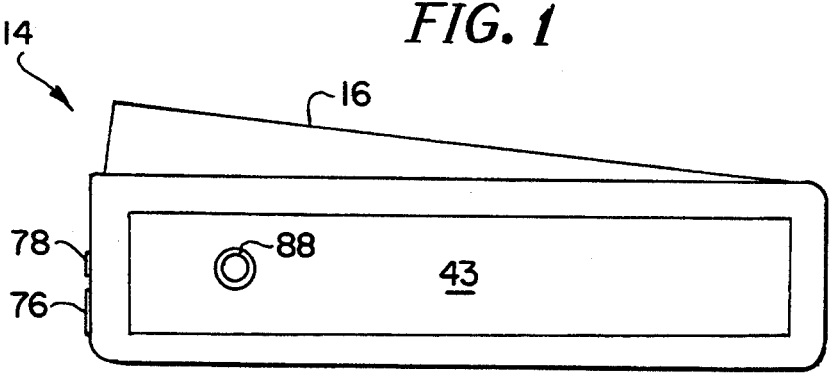
FIG. 2 is a side elevation view of the pump of FIG. 1 showing the lid in open position.
Figure 3:
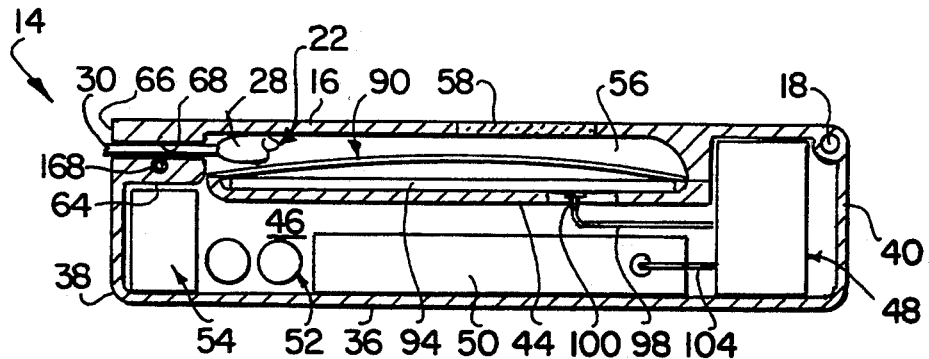
FIG. 3 is a longitudinal section view taken along the line 3—3 of FIG. 1.
Figure 4:
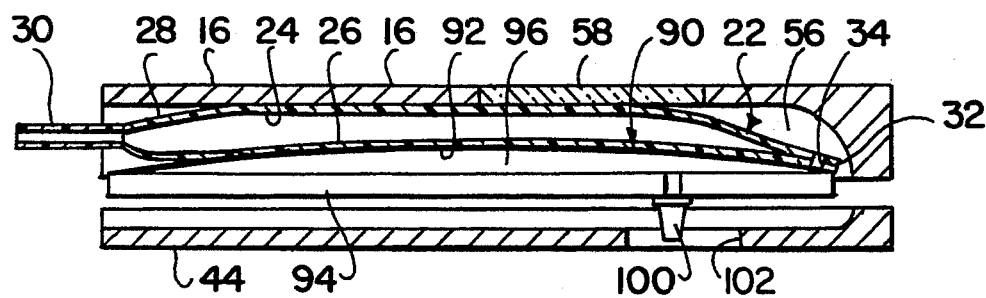
FIG. 4 is a fragmentary longitudinal section view, to an enlarged scale, of the portions of FIG. 3 showing details of the inflatable chamber and compartment in which an IV bag is shown in position.

In the drawings FIGS. 1–3 illustrate at 14 an infusion pump according to a preferred embodiment of the invention. Infusion pump 14 provides an ambulatory system which enables health care professionals to infuse patients directly from standard 50 or 100 ml. single dose container bags which are pre-filled with IV solutions. The infusion pump of the invention is adaptable for use in homes, hospitals or clinics. It is readily adapted for operation in any position, such as resting on a table with the patient in bed, and it could also be carried by the patient.

Infusion pump 14 is comprised of a box-shaped housing 15 having a lid or cover 16 which pivots open and closed about hinges 18 provided on either side of the housing.

The typical IV bag 22 is comprised of a flexible, transparent plastic container with sidewalls 24, 26 of generally rectangular shape. The bag has a front end 28 molded with a pair of necks 30 (one of which is shown) which provide standard filling and dispensing ports. The tail end 32 of the bag (shown as a 50 ml. size bag) is formed with a standard hang hole 34.

Housing 15 is comprised of a bottom wall 36 which carries a front panel 38, rear panel 40 and a pair of side panels 42, 43. A horizontal flat plate 44 is mounted within the housing and extends between the side panels. The plate 44 together with the front and rear panels, side panels and bottom wall define a lower compartment 46 for containing a valve and pump assembly 48, fluid storage reservoir 50, dry cell battery pack 52 and pressure sensor assembly 54. The lower compartment also contains a printed circuit board, not shown, which includes the components for the control system of FIG. 10.

With lid 16 closed as shown in FIG. 3, an upper compartment 56 is formed below the lid and above flat plate 44. Compartment 56 has a size and shape commensurate with a 100 ml. IV bag, and thus can also hold the smaller 50 ml. IV bag. A transparent window 58 is mounted in the lid so that the health care professional can observe the presence or absence of a bag within the upper compartment. The bags are inserted and removed into this compartment from the front of the housing when the lid is moved to the open position shown in FIG. 2. With the lid open and a bag mounted in the compartment, the filling and dispensing ports of the bag seat within a pair of semi-circular grooves 60, 62 that are formed parallel along the upper surface of a lip 64 which protrudes inwardly from the upper edge of the front panel. A downwardly facing boss 66 that is formed on the front end of the lid is also formed with a pair of parallel, semi-circular grooves 68 which are adapted to seat over the upper sides of the filling and dispensing necks when the lid is in the closed position of FIG. 3. Preferably the semi-circular grooves are formed with locking ridges, not shown, in the manner described in copending U.S. application Ser. No. 08/030,782 filed Mar. 12, 1993 by the present inventor.

A power on/off switch 70 and infusion rate switch 72 are mounted on one side of housing front panel 38. On the opposite side of the panel an infusion start switch 74 and reset switch 76 are provided. Digital numeric displays comprising LED's 78 are also provided on the front panel for digital readouts of the cycle timing and IV solution pressure levels which are displayed under influence of the control system. Front panel 38 further mounts an LED 80, preferably of green color, for indicating the Power On/Infusion In Process phase of the operating cycle, an LED 84, preferably red, indicating a Device Malfunction condition, and an LED, preferably orange, indicating a Battery Low condition. Apertures 86 are formed in the middle of the front panel over a suitable speaker, not shown, within the housing for providing audible alarm signals. Sidewall 43 mounts a rechargeable battery/adapter jack 88 for recharging battery pack 52 from an external AC power source.

An inflatable chamber 90 is mounted within upper chamber 56 for applying a uniform force against the lower sidewall of the IV bag for pressurizing the charge of solution contained in the bag. The inflatable chamber is comprised of a rectangular diaphragm 92 which is sealably secured about its perimeter to a rigid bladder frame 94 which in turn is mounted above plate 44. The diaphragm and frame combine to form a bladder having an internal volume 96 for containing a pressurizing fluid. When the contained fluid is pressurized the diaphragm expands upwardly against the lower sidewall of the IV bag, and when fluid is withdrawn elastic memory in the diaphragm moves it down and away from the bag. A diaphragm formed of a latex rubber having a thickness in the range of 0.006" to 0.010" is suitable for this purpose, although other similar materials could be employed. An additional layer of material, such as latex, can be formed over the upper surface of the diaphragm for protecting the IV bags from damage. Bladder frame 94 is formed of a suitable rigid material which prevents the diaphragm from collapsing at its peripheral edges when fluid is withdrawn. An acrylic plastic on the order of $\frac{1}{8}$" thickness is suitable for this purpose.

Fluid is directed into and removed from the inflatable chamber by means of tubing 98 which is connected at one end through a fitting 100 with an opening 102 formed through plate 44 and at its opposite with valve/pump assembly 48. A supply of the fluid is stored in reservoir 50, and this fluid is transferred between the reservoir and the valve/pump assembly through tubing 104. Reservoir 50 can be formed with elastic walls, or it could also be formed with rigid sidewalls. In the illustrated embodiment of the fluid employed for operating the inflatable chamber preferably is a low viscosity, non-toxic liquid such as oil, although other suitable liquids could be employed for this purpose. The invention also contemplates that a gas such carbon dioxide or air could be used to operate the inflatable chamber, as in the embodiment described below in connection with FIG. 12.

The invention also contemplates that the inflatable chamber can be comprised of a suitable bellows, not shown, comprised of a rigid plate which is joined about its perimeter with elastic sidewalls secured at their lower ends about the perimeter frame 94. In this aspect of the invention, pressurized fluid within the bellows moves the rigid plate upwardly for uniform application of force against the lower sidewall of the IV bag, thereby serving to minimize the amount of solution that is left in the bag after the dispensing step is completed.

Figure 5:
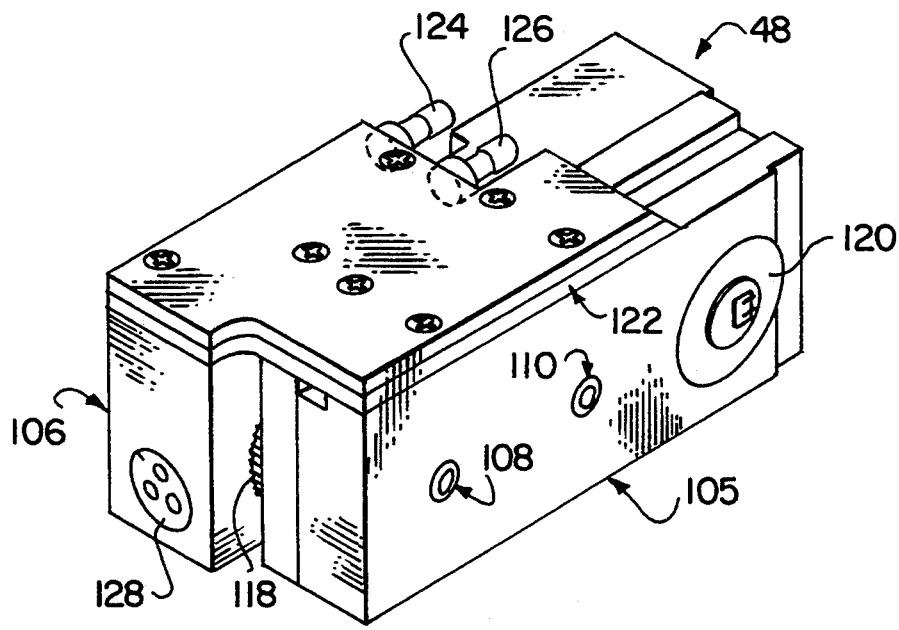
FIG. 5 is a perspective view, to an enlarged scale, of the pump and valve assembly of the infusion pump of FIG. 1.
Figure 6:
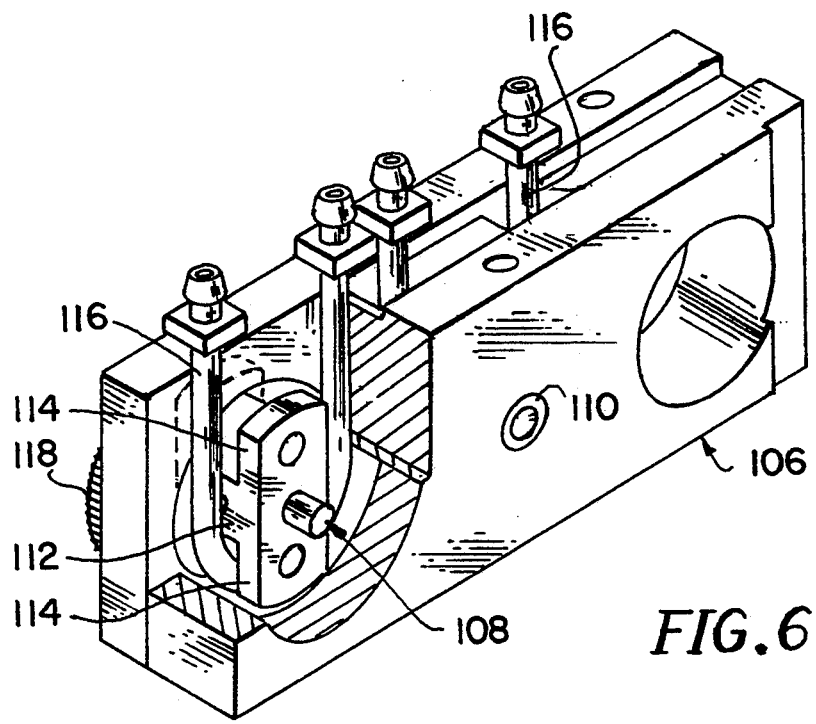
FIG. 6 is a perspective view, partially broken away, showing details of the pump structure for the assembly of FIG. 5.
Figure 7:
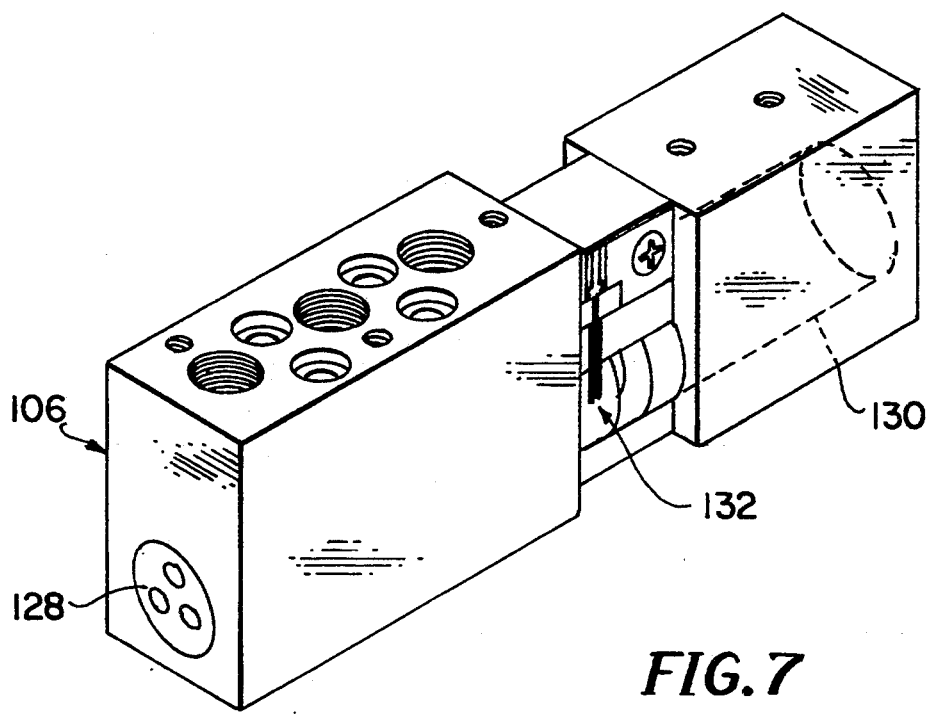
FIG. 7 is a perspective view of the valve block and valve cylinder position sensor arrangement for the assembly of FIG. 5.

Pump/valve assembly 48 is shown in detail in FIGS. 5–7 and includes a pump housing 105 and valve body 106. Housing 105 mounts a pair of pumps 108 and 110 which are of the reversible peristaltic type. Each pump includes a rotor 112 formed with eccentric lobes 114, 114' which, as they rotate, alternately compress portions of U-shaped elastic tubing 116, 116' for pumping the fluid. The pump rotors are turned simultaneously by a gear train 118 which is coupled with an electric motor 120 mounted in one end of the pump housing.

A manifold assembly plate 122 is mounted across the top of both the valve body and pump housing, and the manifold assembly is provided with a pair of inlet/outlet fittings 124, 126 for connecting with the tubing 98 and 104 leading to the inflatable chamber and fluid reservoir. Within the manifold assembly suitable channels, not shown, are provided for directing the fluid flow from U-shaped tubing 116, 116' in the pump housing into channels leading to valve ports 140-144 (FIG. 8) which surround a rotatable valve cylinder 128. The valve cylinder is turned between three operating positions by motor 130 (FIG. 7). Motor 130 is operated under influence of the control circuit of FIG. 10, and electronic position sensors 132 carried by the valve body touch against and sense suitable contacts on the valve cylinder to provide position feedback signals to the control circuit.

Figure 8:
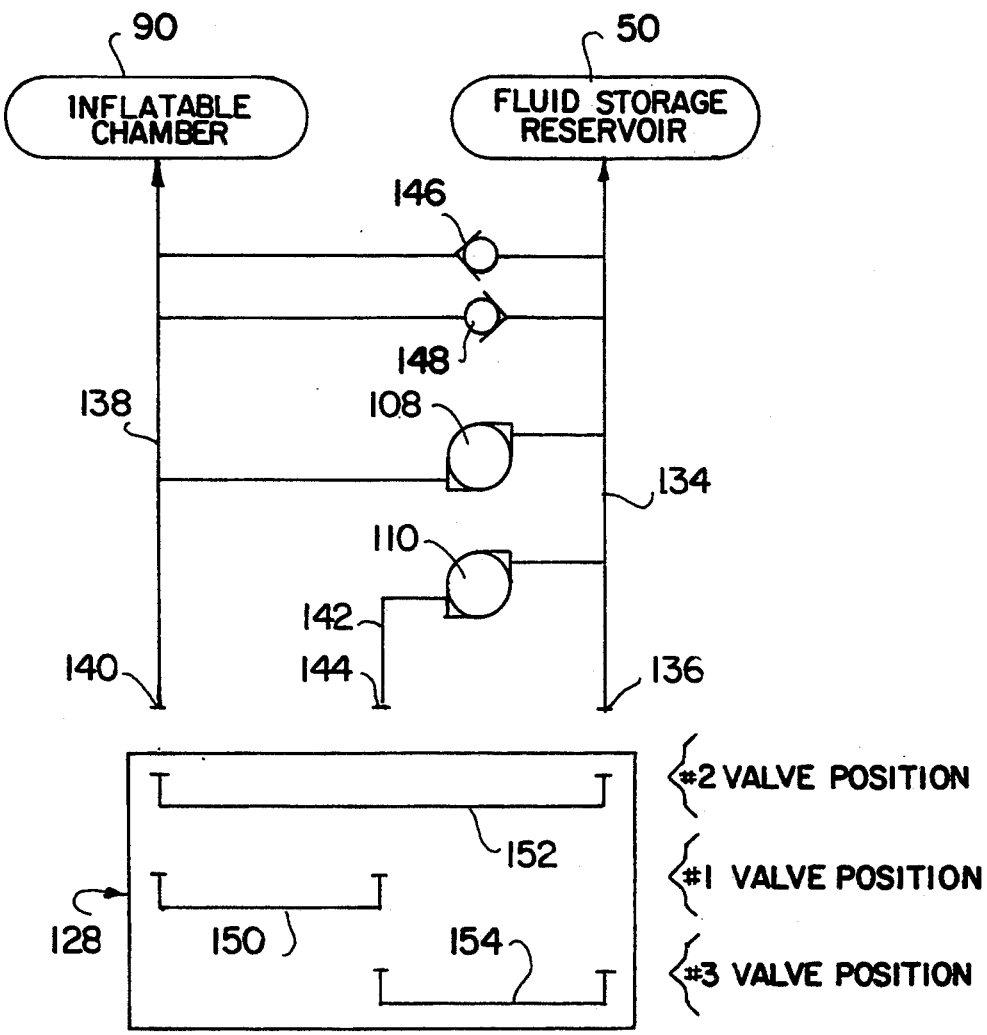
FIG. 8 is a schematic diagram illustrating the hydraulic control system used with the pump and valve assembly of FIG. 5.

FIG. 8 illustrates schematically the valving sequence performed by valve cylinder 128 as it is moved between its three operating positions #1, #2 and #3. In the schematic, manifold 134 is the tubing which connects reservoir 50 with the ports on one side of pumps 108, 110 and with a first port 136 in the valve body 106. Manifold 138 represents the tubing connects inflatable chamber 90 with the ports on the opposite side of the pump and with a second port 140 in the valve body. Line 142 provides a path from pump 110 to a third port 144 in the valve body. A pair of pressure relief valves 146, 148 are provided between the manifolds for preventing overpressure conditions on either of the chamber or reservoir sides.

During the initial or filling phase of operation, valve motor 130 is first actuated to move valve cylinder 128 to its #1 position. The control system of FIG. 10 then actuates motor 120 for operating pumps 108 and 110 in their forward directions for rapidly filling the inflatable chamber. In position #1, the opposite ends of a channel 150 in the cylinder register with valve ports 140 and 144 so that the combined output flow from both pumps is directed through manifold 138 into chamber 90. During this phase both pumps withdraw fluid through manifold 134 from reservoir 50. For the bypass or standby phase, the valve cylinder is turned to its #2 position where the opposite ends of a channel 152 in the cylinder are brought into register with valve ports 136 and 140. The output flow from the pumps, operating either in forward or reverse directions, then recirculates through the channel 152 without either filling or emptying the inflatable chamber or reservoir. During the dispensing phase when it is desired to maintain fluid within the inflatable chamber at a steady pressure, the control system moves the valve cylinder to its #3 position. In this position the opposite ends of a channel 154 within the cylinder are brought into register with valve ports 136 and 144. With both pumps being operated in their forward flow directions, the flow from pump 110 recirculates while the flow from only pump 108 is directed through manifold 138 into the inflatable chamber while withdrawing a supply of fluid from the reservoir. The #1 position of the valve cylinder is used during the emptying phase for pumping fluid from chamber 90 back to reservoir 50 when the pumps are operated in reverse flow direction by the control system.

The invention contemplates that the valve/pump assembly could comprise a single rotor, not shown, in place of the two rotors shown in the illustrated embodiment. In such a case suitable modifications would be made in the valving arrangement and control circuitry by which the single rotor pump would be operated continuously for rapid filling of the chamber during the initial phase, and the pump would then be intermittently turned on and off to maintain the desired pressure level in the chamber for the remainder of the dispensing phase.

Figure 9:
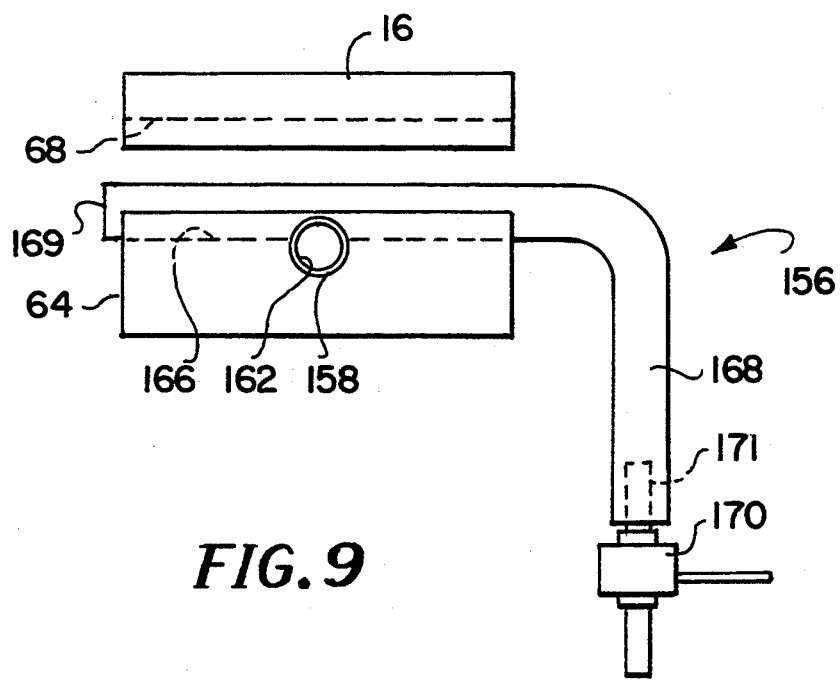
FIG. 9 is a perspective view, to an enlarged scale, showing the arrangement for the non-intrusive sensing pressure of IV solution discharging from an IV bag within the compartment shown in FIG. 3.

FIG. 9 illustrates sensing device 156 for a non-intrusive sensing of IV solution pressure in the flow path leading from the discharge port of the bag. A cannula 158 connected with the dispensing port of the bag is adapted for receiving the spike of a suitable IV tube assembly, not shown. The cannula is seated in the semicircular groove 162 formed in lip 64 on the front panel. A channel 166 is formed transversely through the lip with a lower portion of the channel penetrating into an upper portion of the groove 162. The channel carries an elongate tube or pressure vessel 168 which is formed with an elastic wall. The distal end 169 of the pressure vessel is closed and its proximal end is also closed by a pressure sensor 170. A suitable fluid is confined under static conditions within the pressure vessel. Pressure sensor 170 has a bulb 171 which is exposed to the static fluid within the cannula to convert the fluid pressure level to an electric signal which is directed through suitable leads to the control circuit of FIG. 10. The wall of the pressure vessel is in contact with the wall of the cannula, which is of a suitable elastic material such that the pressure vessel constricts and dilates as the cannula respectively dilates and constricts. An increase in solution pressure from the dispensing port causes cannula 158 to dilate, and this in turn causes pressure vessel 168 to constrict and increase the pressure of static fluid which it contains, and this condition is detected by sensor 170.

Figure 10:
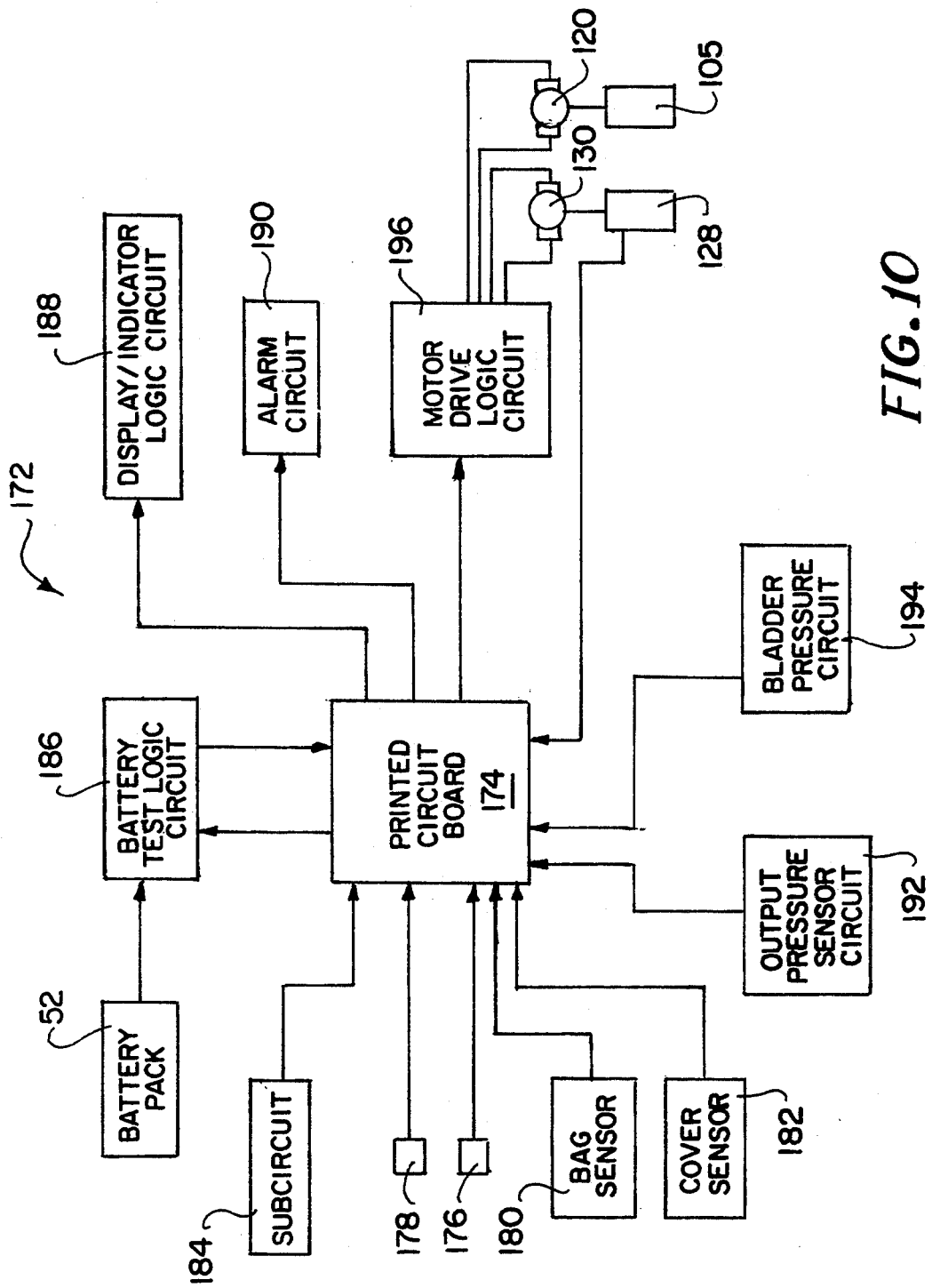
FIG. 10 is schematic diagram of the control system for the infusion pump of FIG. 1.

FIG. 10 schematically illustrates details of control circuit 172 for controlling the operation of the infusion pump. The circuit includes a printed circuit board (PCB) 174 which receives power from battery pack 52. The PCB includes a suitable micro-controller IC chip, not shown, which is programmed with appropriate conventional logic circuits to provide the functions described below in connection with the flow chart of FIGS. 11A through 11F. Lithium battery 176 provides power to the IC chip. Clock timing signals are received from oscillator 178. Bag-in place sensor 180 and cover closed sensor 182, both of which can be similar to that described in co-pending application Ser. No. 08/030,782, are provided and connected with the PCB. Subcircuit 184 connects the PCB with the settings of the front control panels described in connection with FIG. 1. Dry cell battery pack 52 is connected through battery test logic circuit 186 with PCB 174. The PCB is also connected with a display/indicator logic circuit 188 and audible alarm circuit 190. Circuit 192 includes the output pressure sensor 170 described in connection with FIG. 12. A suitable bladder pressure sensor circuit 194 is also connected with the PCB. The PCB drives a motor drive logic circuit 196 which in turn drives pump motor 120 for operating the pumps within pump housing 105 and valve motor 130 for operating valve cylinder 128.

Figure 11A:
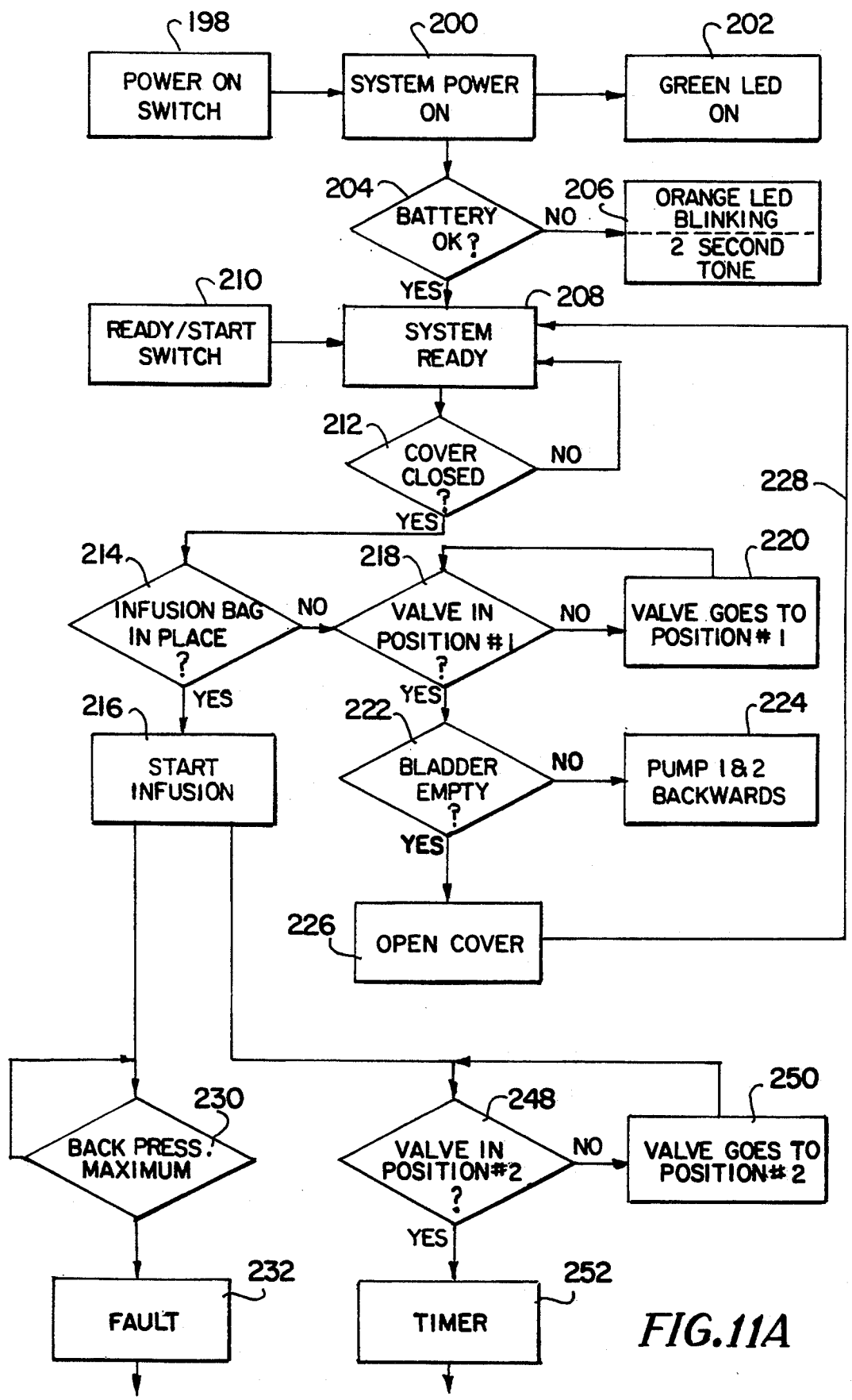
FIGS. 11A through 11C comprise a flow chart illustrating the method steps in the operation of the control system of FIG. 10.
Figure 11B:
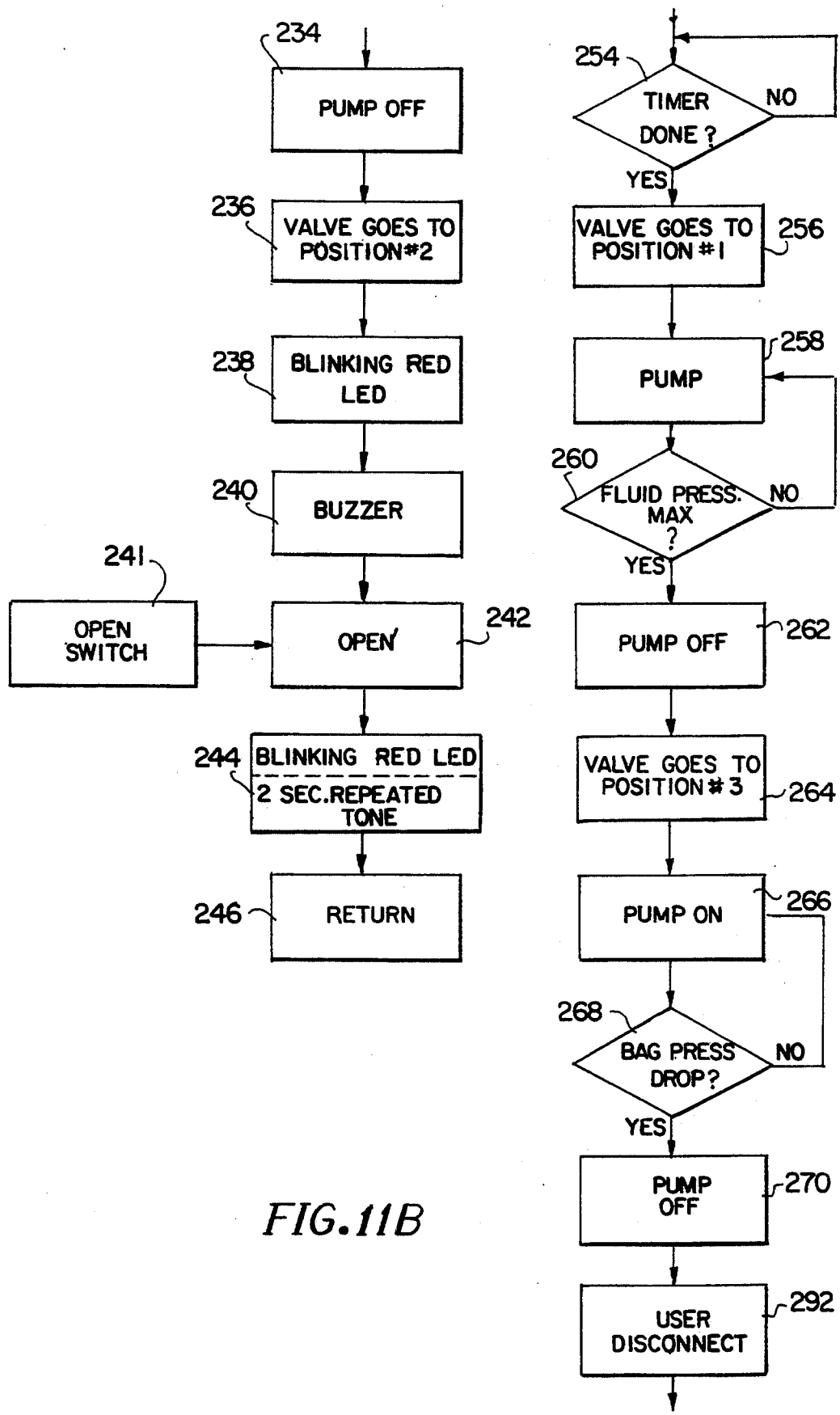

The steps in the method of operation of the control circuit and infusion pump of the invention will be explained in connection with the flow chart of FIGS. 11A through 11C. With power switch 70 turned on at step 198, the logic circuit in the IC chip of PCB 174 senses this condition at step 200 and turns green LED on at step 202. For the next step 204 the circuit checks the battery charge condition. If the charge is below the predetermined level, orange LED blinks and the audible alarm is energized at step 206 to give a two-second duration tone. If the battery charge is adequate, the logic goes to the system ready step 208. At this step if infusion start switch 74 has been turned on by the operator at 210, the circuit checks to determine if the lid or cover is closed. If the sensor detects that the cover is closed at step 212, then the logic proceeds to the infusion bag-in-place step 214. If the bag-in-place switch is closed then the logic proceeds to the infusion process step 216. If the infusion bag is not in place, then the logic proceeds to step 218 which determines, through the position of valve cylinder position sensor 132 shown in FIG. 7, whether the cylinder is in position #1. If not, then the logic proceeds to step 220 where motor 130 is operated to move the valve cylinder to position #1. If yes, then the logic proceeds to step 222 which determines whether the bladder (inflatable chamber) is empty. If not, then the logic proceeds to step 224 for operating both pumps backwards to empty the chamber. If the bladder is empty then the logic proceeds to step 226 to determine whether the cover is open.

With the cover closed a suitable latch, not shown, can be provided to lock the cover in its closed position to prevent accidental removal of the IV bag before the infusion process is completed. If at the start of the infusion process the cover is sensed as being unlatched or open at step 226, then a signal is sent back through line 228 to indicate that the system is not ready at step 208. At the start infusion step 216, the system checks for a fault condition at step 230. This step senses the maximum back pressure on the inflatable chamber or bladder. If a dangerous high pressure condition is sensed then the logic proceeds to fault step 232 which shuts the pump motor off at step 234. Valve cylinder 128 is then turned to position #2 at step 236. The red LED is caused to blink at step 238, and buzzer is activated at step 240. This alerts the health care professional to open the cover at steps 241 and 242, which in turn actuates the red LED and audible alarm at step 244. The fault can then be checked and cleared at step 246.

After the start infusion step, the logic proceeds to step 248 to determine if the valve cylinder is in its bypass position #2. If not then the valve is moved to this position at step 250. At this time the pumps have not yet been actuated, and the elastic wall of reservoir 50 provides sufficient pressure to begin filling the bladder or chamber with fluid. At step 252 a time delay is provided for this initial filling to take place, and the delay is ended at step 254 after a predetermined time on the order of thirty seconds. At the next step 256 the valve cylinder is moved to position #1, and at step 258 the pump motor is operated to drive both pumps in their forward directions to complete the filling phase. Step 260 monitors fluid pressure in the bladder, and at the predetermined maximum pressure the logic proceeds to step 262 which turns the pump motor off. At the next step 264 to begin pressurization for the dispensing phase the valve cylinder is moved to position #3 and the motor is turned on at step 266. While both pumps are driven in a forward direction, only pump 108 is connected to maintain pressure in the bladder. The bag outlet pressure is sensed at step 268, and a drop in pressure below a predetermined level indicates that the bag is empty so that the logic proceeds to step 270 for turning the pump motor off.

At step 292 an audible alarm or light signal on the front panel is activated for indicating to the user that the IV bag is empty, that the dispensing phase is finished and that the patient should be disconnected from the IV tubing. The user can then, at step 294, press reset switch 76 which activates the reset circuit at 296 which in turns operates valve cylinder 128 to bypass position #2 step at 258. The reset switch can also be operated to abort the operation during mid-cycle. With both pumps off the elastic memory of the bladder wall creates sufficient pressure on the fluid to begin emptying the bladder by forcing fluid back to the reservoir until a time delay on the order of thirty seconds is completed at step 300. The valve cylinder is then turned to position #1 at step 302, and the pump motor is actuated to operate both pumps backwards at step 304 for pumping the bladder substantially fully empty. When the fluid pressure in the bladder is sensed at below a predetermined level at step 306, the logic moves to step 308 to shut the pump down. The control circuit then causes yellow LED to blink, and an audible alarm to sound for a two-second duration, both at step 310. This provides an indication to the user that the cover can be opened to remove the spent infusion bag at step 312, thus completing the infusion process.

Figures 11C, 12:
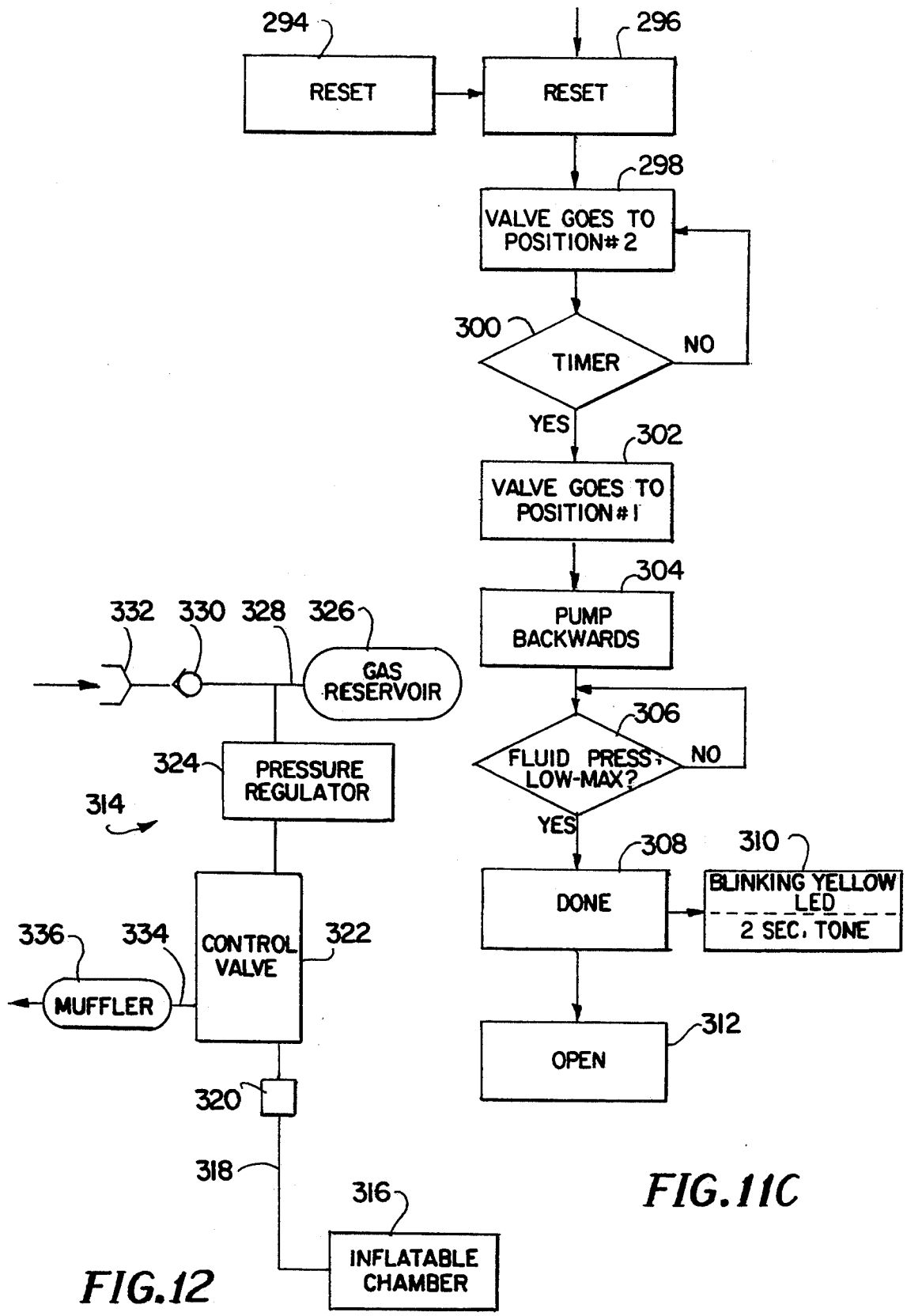
FIG. 12 is a schematic diagram of another embodiment which utilizes gas as the fluid for operating the inflatable chamber of the infusion pump.

FIG. 12 illustrates schematically an embodiment providing a control system 314 for operating an inflatable chamber 316 with gas as the working fluid in place of the liquid pumping system of the embodiment of FIGS. 1–11. Inflatable chamber 316 is connected through line 318 with pressure sensor 320 and control valve 322. Control valve 322 is connected through pressure regulator 324 with a gas reservoir 326 which is mounted on-board the pump housing. A branch line 328 from the gas reservoir leads through check valve 330 to an adapter 332. Standard gas charge cylinders can be temporarily coupled with the adapter for charging the reservoir with a supply of gas, such as $CO_2$, under pressure. Line 334 leads from valve 322 to a muffler 336 for exhausting air either at the end of discharge cycle or when an overpressure condition exists. Valve 332 can comprise a suitable three-way valve operable in one mode for connecting gas reservoir 326 with inflatable chamber 316, and operable in another mode for connecting chamber 316 with muffler 336 and the exhaust line for discharging the chamber at the end of the dispensing phase.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. An infusion pump for use with a flexible bag containing a charge of prepackaged intravenous solution, said bag having a pair of sidewalls and a dispensing port adapted for discharging the solution along a flow path through intravenous tubing for delivery to a patient, the pump comprising the combination of a housing; a compartment within the housing for receiving said bag; an inflatable chamber having a diaphragm which at least partially envelopes the chamber; pressurizing means operable in a delivery mode for directing fluid under pressure into said inflatable chamber for causing said diaphragm to expand, said pressurizing means further being operable in a recovery mode for directing fluid from the inflatable chamber for enabling said diaphragm to contract; and means for positioning the flexible bag at a position within the compartment at which the bag sidewalls are caused to be compressed together responsive to said expansion of the diaphragm for pressurizing said charge of intravenous solution with the pressurized intravenous solution being discharged through the dispensing port.

2. An infusion pump as in claim 1 in which said fluid is comprised of a liquid.

3. An infusion pump as in claim 1 in which said fluid is comprised of a gas.

4. An infusion pump as in claim 1 in which said inflatable chamber is comprised of a bladder which forms said diaphragm, said bladder being comprised of a material having elastic shape memory with the bladder contracting under influence of its said elastic shape memory when said fluid is being directed from the chamber.

5. An infusion pump as in claim 1 in which said inflatable chamber is comprised of a bellows having a substantially rigid plate which forms said diaphragm and which moves in a direction to push against a sidewall of the bag responsive to said fluid under pressure within the chamber.

6. An infusion pump as in claim 1 which includes pressure sensing means for sensing the pressure level of the intravenous solution being discharged from the inflatable chamber; and control means for controlling the pressure of fluid within the inflatable chamber responsive to said pressure level of the intravenous solution for thereby controlling the rate of discharge of solution through said intravenous tubing.

7. An infusion pump for use with a flexible bag containing a charge of prepackaged intravenous solution, said bag having a pair of sidewalls and a dispensing port adapted for discharging the solution along a flow path through intravenous tubing for delivery to a patient, said pump comprising the combination of a compartment for receiving said bag; a storage reservoir for containing a supply of fluid; an inflatable chamber having a diaphragm which at least partially envelopes the chamber; pump means operable in a delivery mode for pumping fluid under a predetermined pressure from said storage reservoir into said inflatable chamber for causing said diaphragm to expand; and means for positioning the flexible bag at a position within the compartment at which the bag sidewalls are caused to be compressed together responsive to said expansion of the diaphragm for pressurizing said charge of intravenous solution with the pressurized solution being discharged through the dispensing port.

8. An infusion pump as in claim 7 which includes control means for controlling the flow of said fluid from the storage reservoir into said inflatable chamber at a predetermined first rate and at a predetermined first pressure for rapid filling of the inflatable chamber during a first phase of said delivery mode, said control means further controlling said flow of fluid at a second pressure greater than said first pressure during a second phase of said delivery mode for bringing the fluid pressure within the chamber to a magnitude which is effective for discharging the solution through the dispensing port.

9. An infusion pump as in claim 8 in which said control means includes means operable in a recovery mode for directing fluid from the inflatable chamber to the reservoir for enabling said diaphragm to contract.

10. An infusion pump as in claim 7 which includes pressure sensing means for sensing the pressure level of the intravenous solution being discharged from the inflatable chamber; and said control means includes means for controlling the pressure of fluid within the inflatable chamber responsive to said pressure level of the intravenous solution for thereby controlling the rate of discharge of intravenous solution through said intravenous tubing.

11. An infusion pump as in claim 10 in which said pressure sensing means includes means for sensing said pressure level of the intravenous solution without intrusion into said solution flow path.

12. An infusion pump as in claim 11 which includes a cannula for confining a portion of said flow path of the intravenous solution with the cannula having a first elastic wall which dilates and constricts responsive to a respective increase and decrease of said pressure level of the intravenous solution; said means for sensing said pressure level comprises a pressure vessel filled with a static fluid and having a second elastic wall; means for positioning the second elastic wall of the pressure vessel in juxtaposed relation with the first elastic wall of the cannula whereby said dilation and constriction of the cannula causes said second elastic wall of the pressure vessel to respectively constrict and dilate for respectively increasing and decreasing the pressure of the static fluid within the pressure vessel; and sensor means for sensing the pressure of the static fluid within the pressure vessel.

13. A method of infusing intravenous solution from a flexible bag with the bag having a pair of sidewalls and a dispensing port adapted for discharging the solution along a flow path through intravenous tubing for delivery to a patient, the method comprising the steps of holding the bag with a charge of intravenous solution contained therein against the diaphragm of an expandable chamber; pressurizing a fluid within said chamber to a pressure level sufficient to cause said chamber to expand; moving said diaphragm against the bag and compressing said sidewalls together responsive to said expansion of the chamber; pressurizing said charge of solution within the bag responsive to compression of the bag sidewalls; and discharging said solution under pressure out through said dispensing port along said flow path and through said intravenous tubing.

14. A method as in claim 13 in which said step of pressurizing the fluid includes pumping the fluid at a first rate of flow and first pressure for an initial rapid filling phase into the chamber; and thereafter pumping the fluid at a second rate of flow less than said first rate and at a second pressure greater than said first pressure for another phase for bringing the fluid in the chamber to a pressure level which is effective for discharging the fluid through the dispensing port.

15. A method as in claim 13 which includes the steps of directing fluid from the chamber to a storage reservoir for enabling the chamber to contract during a recovery mode; and moving the diaphragm away from the bag responsive to said contraction of the chamber.

16. A method as in claim 13 which includes the steps of sensing the pressure of said intravenous solution being discharged from the bag; and controlling the pressure of fluid within the chamber at a level, responsive to said sensed solution pressure, which is sufficient to regulate the flow rate of solution through the intravenous tubing.

17. A method as in claim 16 in which said step of controlling the pressure of fluid within the chamber comprises directing said discharged solution through a cannula having a first elastic wall; dilating and constricting said first elastic wall responsive to a respective increase and decrease of solution pressure within the cannula; providing a pressure vessel having a second elastic wall which confines a static fluid and positioning the second elastic wall in juxtaposed relationship with the first elastic wall of the cannula; constricting and dilating the second elastic wall of the pressure vessel responsive to respective dilation and constriction of the first elastic wall of the cannula; sensing the pressure of the static fluid within the pressure vessel as it varies in response to said constriction and dilation of the second elastic wall to thereby provide an indirect pressure signal of said solution pressure; and controlling said level of pressure within the chamber responsive to said sensed pressure of the static fluid.

* * * * *